United States Patent
Kubo et al.

(10) Patent No.: US 11,733,235 B2
(45) Date of Patent: Aug. 22, 2023

(54) METHOD FOR EVALUATING IMMUNOGENICITY OF TEST SUBSTANCE

(71) Applicant: Chugai Seiyaku Kabushiki Kaisha, Tokyo (JP)

(72) Inventors: Chiyomi Kubo, Shizuoka (JP); Shigeki Motoyama, Shizuoka (JP); Yoshiyuki Arata, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 1001 days.

(21) Appl. No.: 16/471,834

(22) PCT Filed: Dec. 26, 2017

(86) PCT No.: PCT/JP2017/046517
§ 371 (c)(1),
(2) Date: Jun. 20, 2019

(87) PCT Pub. No.: WO2018/124005
PCT Pub. Date: Jul. 5, 2018

(65) Prior Publication Data
US 2020/0191770 A1    Jun. 18, 2020

(30) Foreign Application Priority Data

Dec. 27, 2016  (JP) ................................ 2016-252235

(51) Int. Cl.
*G01N 33/50* (2006.01)
*C12Q 1/06* (2006.01)
*G01N 33/15* (2006.01)

(52) U.S. Cl.
CPC ............ *G01N 33/505* (2013.01); *C12Q 1/06* (2013.01); *G01N 33/15* (2013.01); *G01N 2333/55* (2013.01)

(58) Field of Classification Search
None
See application file for complete search history.

(56) References Cited

U.S. PATENT DOCUMENTS

| 7,868,139 B2 | 1/2011 | Elson et al. |
| 2010/0129386 A1 | 5/2010 | Elson et al. |
| 2015/0177253 A1 | 6/2015 | Steck et al. |

FOREIGN PATENT DOCUMENTS

| AU | 2015215938 A1 | 9/2015 |
| JP | 2009528044 A | 8/2009 |
| WO | WO-2007099341 A1 | 9/2007 |
| WO | WO2008100598 A2 | 8/2008 |
| WO | WO2014093622 A2 | 6/2014 |

OTHER PUBLICATIONS

Jaber (Journal of Pharmaceutical and Biomedical Analysis, 2007, vol. 43, pp. 1256-1261). (Year: 2007).*
Jung (Journal of Immunological Methods, 1993, vol. 159, No. 1-2, pp. 197-207). (Year: 1993).*
Ahmadi, M., et al., "Small Amounts of Sub-Visible Aggregates Enhance the Immunogenic Potential of Monoclonal Antibody Therapeutics," Pharm Res, 32:1383-1394 (2015).
Delluc, S., et al., "Quantitative analysis of the CD4 T-cell repertoire specific to therapeutic antibodies in healthy donors," FASEB J 25:2040-2048 (2011).
Jawa, V., et al., "T-cell dependent immunogenicity of protein therapeutics: Preclinical assessment of mitigation," Clinical Immunology 149:534-555 (2013).
Joubert, M. K., et al., "Use of In Vitro Assays Immunogenicity Risk of Antibody-Based Biotherapeutics," PLOS ONE, 11(8):e0159328 (2016), 22 pages.
Letourneau, S., et al., "IL-2- and CD25-dependent immunoregulatory mechanisms in the homeostatis of T-cell subsets," J Allergy Clin Immunol, 123:758-762 (2009).
Wuest, S. C., et al., "A role for interleukin-2 trans-presentation in dendritic cell-mediated T cell activation in humans, as revealed by daclizumab therapy," Nature Medicine 17(5):604-609 (2011).

* cited by examiner

*Primary Examiner* — Celine X Qian
(74) *Attorney, Agent, or Firm* — Nixon & Vanderhye P.C.

(57) ABSTRACT

In one aspect, disclosed herein is a method for evaluating the immunogenicity of a test substance in a short period of time by using, as an indicator of the immunogenicity of the test substance, the proportion of IL-2-secreting cells in a T cell population (preferably a CD4$^+$ T cell population) at a time point during the early stage of IL-2 secretion after stimulation of the T cell population with the test substance (preferably 24 hours to 72 hours after the stimulation with the test substance).

10 Claims, 5 Drawing Sheets

METHOD FOR EVALUATING IMMUNOGENICITY OF TEST SUBSTANCE

CROSS-REFERENCE TO RELATED APPLICATIONS

This application is a U.S. National Phase of PCT Application No. PCT/JP2017/046517, filed Dec. 26, 2017, which claims the benefit of Japanese Patent Application No. 2016-252235, filed Dec. 27, 2016, each of which is incorporated herein by reference in its entirety.

TECHNICAL FIELD

The present invention relates to methods for evaluating immunogenicity which are characterized by when and how to detect IL-2 in IL-2-secreting cells. Furthermore, the present invention relates to methods for screening for pharmaceutical candidate substances which are characterized in that test substances are evaluated for immunogenicity.

BACKGROUND

Today, many pharmaceuticals having complex structures such as proteins are available on the market. In a human body, entry of a foreign substance into the body causes immune responses, and also in the field of pharmaceuticals, a protein-derived active ingredient may be recognized as a foreign protein in the immune responses, and the action of such a pharmaceutical as an antigen may lead to production of anti-drug antibodies (ADAs). ADA production may have unfavorable effects such as decrease in therapeutic effects of the pharmaceuticals, and in some cases, may elicit immune responses that can be life-threatening.

Therefore, in the development of pharmaceuticals containing a protein-derived active ingredient, a large number of test substances need to be evaluated for their immunogenicity from early stages of the development. Thus, studies have been conducted on methods for selecting less immunogenic test substances as candidate substances by screening. A known approach is an assaying method in which human tissue-derived cells are stimulated with a test substance and the substance is evaluated using as an indicator the proliferation of T cells induced by immune response or the number of cells that produce cytokines such as IL-2 when the cell proliferation is active (for example, see Patent Document 1 and Non-patent Document 1).

In connection with T cell activation, the roles of IL-2 production and IL-2 receptor a (CD25) expression have been reported (see for example, Non-patent Document 2). In this report, co-culture of T cells with dendritic cells stimulated with a peptide derived from maltose-binding protein (MBP), which is known to have very strong immunogenicity, resulted in induction of IL-2 production and T cell proliferation; however, when the cells were not co-cultured or when an anti-IL-2 receptor a (CD25) antibody was added to the dendritic cells before co-culture, almost no IL-2 production or cell proliferation was detected even with stimulation with the peptide. There are also reports that T cells that respond to stimulation with a less immunogenic substance like a protein formulation (for example, an antibody formulation) are very few (Non-patent Documents 3 and 4). In fact, it has been reported that few donors produce cytokines in response to stimulation with a protein formulation at the stage before active T cell proliferation, and that it depends on the protein formulation used for the stimulation how much specific T cells proliferate in response to the stimulation and what the frequency of donors is who show cytokine production in association with the cell proliferation (Non-patent Document 1). Thus, the proliferation of T cells induced by immune response to a test substance, and the production of cytokines when the cells are proliferating actively, are drawing attention as indicators for assessing the immunogenicity of the test substance.

Reference documents cited herein are listed below. Contents described in these documents are incorporated herein by reference in their entirety. This is not admission that any of these documents is prior art to the present description.

CITATION LIST

Patent Document

JP-A (Kohyo) 2009-528044

Non-Patent Documents

PLoS One. 2016 Aug. 5; 11(8):e0159328.
Nat Med. 2011 May; 17(5): 604-609.
FASEB J. 2011 June; 25(6):2040-2048.
Clin Immunol. 2013 December; 149(3):534-555.

SUMMARY

Problems to be Solved

In conventional methods in which the immune response of T cells is used to evaluate the immunogenicity of a test substance or to screen test substances for a pharmaceutical candidate substance, the evaluation or screening is performed at a time when T cells are proliferating actively (five to seven days or later after initiation of culture in the presence of the test substance). Therefore, it takes a certain period of time or longer in order that the T cell proliferation can be detected at the protein level. Accordingly, from the aspect of efficiency, the conventional methods are not adequate as a process for selecting candidate substances suitable for pharmaceuticals. An objective of the present invention is to achieve the evaluation of immunogenicity in a short time after initiation of culture in the presence of a test substance.

Accordingly, the present inventors conducted dedicated studies to identify early-stage markers useful for evaluating immunogenicity or screening for pharmaceutical candidate substances. Thus, an objective of the present invention is to provide an indicator suitable for evaluating the immunogenicity of a test substance or screening for pharmaceutical candidate substances at the stage before the T cell proliferation becomes active in the T cell immune response (less than five days after initiation of culture in the presence of a test substance). Another objective of the present invention is to provide methods for evaluating the immunogenicity of a test substance or screening for pharmaceutical candidate substances in a short period of time in the T cell immune response. Furthermore, the present invention provides methods for selecting candidate substances from among test substances in an efficient and low-cost manner by shortening the time of each cycle necessary for evaluating the immunogenicity of the test substances or for screening the test substances for pharmaceutical candidate substances and thereby allowing for more trial-and-error processes.

Means for Solving the Problems

To achieve the above-mentioned objectives, the present inventors carried out dedicated studies on indicators useful for shortening the period of time taken for evaluation of immunogenicity, when and how those indicators can be detected, and how to efficiently screen for candidate substances. As a result, the inventors discovered that IL-2 secreted in the initial response stage before T cell proliferation becomes active (less than five days after initiation of culture in the presence of a test substance) is surprisingly useful as an indicator for evaluating immunogenicity, and discovered methods for detecting IL-2-secreting cells which are present only in very small numbers at that stage, and methods of screening for candidate substances in an efficient and low cost manner by carrying out the whole evaluation system in a short period of time. The present inventors have thus completed the present invention.

The present invention provides the following inventions:

[1] a method for evaluating immunogenicity of a test substance, the method comprising the steps of:
(a) culturing a blood-derived cell population with a test substance, wherein the blood-derived cell population comprises antigen-presenting cells (APCs) and $CD4^+$ T cells and does not substantially comprise $CD8^+$ T cells or $CD25^+$ T cells;
(b) detecting IL-2-secreting T cells in the cell population cultured in step (a) at a time point during the early stage of IL-2 secretion; and
(c) calculating the proportion of the IL-2-secreting T cells detected in step (b);

[2] the method of [1], wherein the blood-derived cell population is a cell population derived from peripheral blood mononuclear cells (PBMCs);

[3] the method of [1] or [2], wherein the blood is derived from a human;

[4] the method of any one of [1] to [3], wherein the time point during the early stage of IL-2 secretion is before proliferation of the T cells becomes active;

[5] the method of any one of [1] to [4], wherein the time point during the early stage of IL-2 secretion is between 24 hours and 72 hours after initiation of the culturing;

[6] the method of any one of [1] to [5], wherein the test substance is selected from the group consisting of a protein, a peptide, a nucleic acid, a carbohydrate, a lipid, a vaccine, and a conjugate of two or more thereof, and a mixture comprising a combination of two or more thereof;

[7] the method of any one of [1] to [5], wherein the test substance is a protein;

[8] the method of any one of [1] to [5], wherein the test substance is an antibody; and

[9] the method of any one of [1] to [8], wherein the calculating the proportion of the IL-2-secreting cells is measuring the number of the cells by flow cytometry.

The present invention also provides the following inventions:

[10] the method of any one of [1] to [9], the method further comprising the step of determining that the test substance has low immunogenicity if the proportion of IL-2-secreting T cells calculated in step (c) is equivalent to or lower than a control level;

[11] the method of [10], wherein the control level is the proportion of IL-2-secreting T cells calculated in step (c) when the cell population is cultured in the presence of a substance known to have low immunogenicity (low-immunogenicity control level);

[12] the method of any one of [1] to [9], the method further comprising the step of determining that the test substance has high immunogenicity if the proportion of IL-2-secreting T cells calculated in step (c) is equivalent to or higher than a control level;

[13] the method of [12], wherein the control level is the proportion of IL-2-secreting T cells calculated in step (c) when the cell population is cultured in the presence of a substance known to have high immunogenicity (high-immunogenicity control level);

[14] the method of [10] or [12], wherein the control level is the proportion of IL-2-secreting T cells calculated in step (c) when the cell population of step (a) is cultured in the absence of the test substance (negative control level);

[15] the method of any one of [1] to [9], the method further comprising the step of selecting the test substance as a pharmaceutical candidate substance if the proportion of IL-2-secreting T cells calculated in step (c) is lower than a control level;

[16] the method of any one of [1] to [9], the method further comprising the step of determining that a donor (subject from whom the blood-derived cell population has been obtained) is highly responsive to immunotherapy with the test substance if the proportion of IL secreting T cells calculated in step (c) is higher than a control level;

[17] the method of any one of [1] to [9], wherein a donor for whom the proportion of the detected IL-2-secreting T cells calculated in step (c) is higher than a control level is defined as a positive donor, and wherein the method further comprises the step of using the proportion of positive donors in the total number of donors in the same assay as an indicator for evaluating immunogenicity;

[18] use of an IL-2-secreting T cell for evaluating immunogenicity of a test substance;

[19] an IL-2-secreting T cell, which is for use in evaluating immunogenicity of a test substance;

[20] a method for evaluating immunogenicity, wherein a proportion of IL-2-secreting T cells is used as an indicator;

[21] a method of screening for a pharmaceutical candidate substance, the method comprising selecting a test substance evaluated as having low immunogenicity in the method of any one of [1] to [9] as a pharmaceutical candidate substance;

[22] a method of measuring the proportion of IL-2-secreting CD4+ T cells in a cell population cultured with a test substance, the method comprising the steps of:
(a) culturing a blood-derived cell population with a test substance, wherein the blood-derived cell population comprises antigen-presenting cells (APCs) and CD4+ T cells and does not substantially comprise CD8+ T cells or CD25+ T cells;
(b) detecting IL-2-secreting T cells in the cell population cultured in step (a) at a time point during the early stage of IL-2 secretion; and
(c) calculating the proportion of the IL-2-secreting T cells detected in step (b),
wherein the method is for evaluating immunogenicity of the test substance;

[23] a method for selecting a substance (modified substance) with reduced immunogenicity or a method for evaluating whether immunogenicity of a modified substance has been reduced, the method comprising the steps of:
(a) culturing a blood-derived cell population with a modified substance or a non-modified substance`e, wherein the blood-derived cell population comprises antigen-presenting cells (APCs) and CD4+ T cells and does not substantially comprise CD8+ T cells or CD25+ T cells;
- (b) detecting IL-2-secreting T cells in the cell population cultured in step (a) at a time point during the early stage of IL-2 secretion;
- (c) calculating the proportion of the IL-2-secreting T cells detected in step (b); and
- (d) determining that the immunogenicity of the modified substance has been reduced if the proportion of IL-2-secreting T cells calculated in step (c) when the cell population is cultured with the modified substance is lower than the proportion when the cell population is cultured with the non-modified substance;

[24] a method of screening for a pharmaceutical candidate substance, the method comprising the steps of:
- (a) culturing a blood-derived cell population with a test substance, wherein the blood-derived cell population comprises antigen-presenting cells (APCs) and CD4+ T cells and does not substantially comprise CD8+ T cells or CD25+ T cells;
- (b) detecting IL-2-secreting T cells in the cell population cultured in step (a) at a time point during the early stage of IL-2 secretion;
- (c) calculating the proportion of the IL-2-secreting T cells detected in step (b); and
- (d) selecting the test substance as a pharmaceutical candidate substance if the proportion of IL-2-secreting T cells calculated in step (c) is lower than the control level;

[25] a method for predicting response of a subject to immunotherapy with a test substance, the method comprising the steps of:
- (a) culturing a cell population with a test substance, wherein the cell population is derived from blood obtained from a subject, and wherein the cell population comprises antigen-presenting cells (APCs) and CD4+ T cells and does not substantially comprise CD8+ T cells or CD25+ T cells;
- (b) detecting IL-2-secreting T cells in the cell population cultured in step (a) at a time point during the early stage of IL-2 secretion;
- (c) calculating the proportion of the IL-2-secreting T cells detected in step (b); and
- (d) determining that the responsiveness of the subject to immunotherapy with the test substance is high if the proportion of IL-2-secreting T cells calculated in step (c) is higher than the control level; and

[26] a kit for evaluating immunogenicity of a test substance, the kit comprising an IL-2-detection reagent and a control substance with a known level of immunogenicity.

Effects of the Invention

The present invention can provide methods that shorten the period of time taken to evaluate the immunogenicity of a test substance or the period of time taken to screen for a pharmaceutical candidate substance in T cell immune response.

Furthermore, the present invention can provide methods for selecting candidate substances from among test substances in an efficient and low-cost manner by shortening the time of each cycle necessary and by allowing for more trial-and-error processes for evaluating immunogenicity of the test substance or for screening for a pharmaceutical candidate substance.

BEST MODE FOR CARRYING OUT THE INVENTION

The present invention relates to methods for evaluating immunogenicity based on the proportion of IL-2-secreting T cells. More specifically, the present invention relates to methods for evaluating immunogenicity of a test substance by using as an indicator the proportion of IL secreting T cells in a cell population cultured with a test substance, preferably using the proportion of IL-2-secreting T cells at a time point during the early stage of IL-2 secretion, more preferably using the proportion of IL-2-secreting T cells before the period when T cell proliferation is active (less than five days after initiation of culture and preferably 24 to 72 hours after initiation of culture in the presence of a test substance, for example, 24 to 67 hours, 24 to 62 hours, 24 to 48 hours, 24 to 42 hours, 42 to 72 hours, 42 to 67 hours, 42 to 62 hours, 42 to 48 hours, 48 to 72 hours, 48 to 67 hours, 48 to 62 hours, 62 to 72 hours, 62 to 67 hours, or 67 to 72 hours after initiation of culture), and even more preferably using the proportion of IL-2-secreting T cells approximately 42 hours to approximately 72 hours after initiation of culture in the presence of a test substance or particularly preferably approximately 48 hours to approximately 67 hours after initiation of culture in the presence of a test substance.

In the context of the present invention, the phrase "the period when T cell proliferation is active" can be rephrased, for example, as the period when antigen-specific T cells can proliferate independently of the antigen, or the period when T cells have differentiated towards expression of their function.

In the context of the present invention, the "test substance" is not particularly limited as long as it is a substance to be evaluated for immunogenicity, but includes, for example, proteins (such as antibodies or vaccines), non-proteins (for example, non-protein high-molecular-weight or low-molecular-weight compounds, including peptides, nucleic acids, carbohydrates, lipids, or vaccines), conjugates of a protein and a non-protein (for example, glycosylated antibodies), and conjugates of a non-protein and a non-protein (for example, glycolipids or peptide-nucleic acid conjugates), and mixtures of a combination of two or more thereof. The two or more thereof to be combined may belong to the same category or different categories, and are not limited. Examples of the test substances in the present invention may include antibodies, peptides, vaccines, immune complexes, adjuvants, blood components, and impurities such as endotoxins that may contaminate formulations. In certain embodiments of the present invention, the test substance is an antibody.

In the context of the present invention, a cell population to be cultured with a test substance is a blood-derived cell population which contains antigen-presenting cells (APCs) and $CD4^+$ T cells and does not substantially contain $CD8^+$ T cells (cytotoxic T cells) or $CD25^+$ T cells (CD25-positive activated T cells and/or regulatory T cells). Preferably, for example, it is a cell population derived from peripheral blood mononuclear cells (PBMCs) which contains antigen-presenting cells (APCs) and $CD4^+$ T cells and does not substantially contain $CD8^+$ cells or $CD25^+$ cells. The aforementioned blood is preferably derived from a mammal, and is particularly preferably derived from a human. Therefore, the IL-2 to be detected is preferably mammalian IL-2, and is particularly preferably human IL-2. The aforementioned blood may be fresh blood or stored blood such as frozen blood. From the viewpoint of ease of availability, stored blood is preferred, and frozen blood is particularly preferred.

Methods for removing $CD8^+$ T cells and $CD25^+$ T cells from a blood-derived cell population are known to those skilled in the art. For example, as described in the Examples herein, the removal can be performed using an anti-CD8 antibody and an anti-CD25 antibody. On the other hand, a cell population of blood from which $CD8^+$ T cells and $CD25^+$ T cells have been removed in advance can also be used for the methods of the present invention. Alternatively, a cell population prepared by adding $CD4^+CD25^-$ T cells to a blood-derived cell population which does not substantially contain $CD8^+$ T cells or $CD25^+$ T cells can also be used. Therefore, the methods of the present invention may include the step of removing $CD8^+$ T cells and $CD25^+$ T cells from a blood-derived cell population, the step of providing a blood-derived cell population from which $CD8^+$ T cells and $CD25^+$ T cells have been removed, or the step of providing a cell population prepared by adding $CD4^+CD25^-$ T cells to a cell population which does not substantially contain $CD8^+$ T cells or $CD25^+$ T cells.

In the present invention, the aforementioned cell population can be cultured by a method known to those skilled in the art. For example, the culture can be performed by the method described in the Examples herein, without limitation thereto. Preferably, the cell population is prepared at $1\times10^6$ cells/mL in OpTmizer CTS T-cell Expansion SFM (Gibco), seeded at 1 mL/well into a 24-well flat-bottomed plate, and preincubated at 37° C. in a 5% $CO_2$ incubator for one hour. Subsequently, a test substance is added, and the cell population is cultured until a time point suitable for evaluation. When the suitable time point is reached, IL-2 catch reagent (IL-2 secretion assay kit, Miltenyi Biotec) is added at 10 μL/well, and the culture is continued for one more hour.

In the present invention, a donor refers to a subject from whom the blood-derived cell population has been obtained.

In the present invention, the proportion of IL-2-secreting T cells to be used as an indicator for evaluating immunogenicity is the proportion of IL-2-secreting T cells in the total cells cultured with the test substance. For example, it is the proportion of IL-2-secreting $CD4^+$ T cells (numerator) in the total $CD4^+$ T cells (denominator) included in the culture system at the time of detecting the IL-2-secreting $CD4^+$ T cells.

In the present invention, the proportion of IL-2-secreting T cells to be used as the indicator for evaluating immunogenicity is preferably the proportion of IL-2-secreting T cells at a time point in the early stage of IL-2 secretion, more preferably the proportion of IL-2-secreting T cells before T cell proliferation becomes active (less than five days after initiation of culture in the presence of a test substance), particularly preferably the proportion of IL-2-secreting T cells approximately 24 hours to approximately 72 hours after initiation of culture in the presence of a test substance, or most preferably the proportion of IL-2-secreting $CD4^+$ T cells approximately 48 hours to approximately 67 hours after initiation of culture in the presence of a test substance.

In the present invention, the term "antibody" is used in the broadest sense and encompasses various antibody structures so long as they exhibit a desired antigen-binding activity, including but not limited to monoclonal antibodies, polyclonal antibodies, multispecific antibodies (for example, bispecific antibodies), and antibody fragments.

An "antibody fragment" refers to a molecule that is not an intact antibody but contains a portion thereof that binds to an antigen the intact antibody binds to. Examples of an antibody fragment include but are not limited to Fv, Fab, Fab', Fab'-SH, and F(ab')2; diabodies; linear antibodies; single-chain antibody molecules (for example, scFv); and multispecific antibodies formed from antibody fragments.

In the present invention, IL-2-secreting T cells can be detected by methods known to those skilled in the art. For example, as described in the Examples herein, IL-2-positive cells labeled with a commercially available IL-2 detection reagent can be detected using flow cytometry.

In the present invention, the immunogenicity of a test substance can be evaluated by comparing the calculated proportion of IL-2-secreting T cells to an appropriate control level. In the context of the present invention, a "control level" can also be referred to as a control value, reference value, or standard value. For example, the mean or median of the proportion of IL-2-secreting T cells detected in the aforementioned cell population cultured in the presence of an appropriate reference substance (control substance), or a predetermined range around that value (for example, mean+/−standard deviation), can be used as a control level. The control level can be determined based on a value measured in parallel with assaying a test substance or a value measured in advance. When a control level is determined based on a value measured in advance, the control level is preferably determined based on a value measured in advance under the same or equivalent conditions as those for assaying the test substance.

In an embodiment of the present invention, the proportion of IL-2-secreting T cells in a cell population cultured in the presence of a substance that has been found to have low immunogenicity by another immunogenicity evaluation method (for example, a drug that yields low anti-drug antibody incidence in a clinical trial or a substance having low $CD4^+$ T cell proliferation-inducing ability) can be used as a control level in evaluating immunogenicity. This control level can be referred to as "low-immunogenicity control level". In that case, when the proportion of IL-2-secreting T cells in a cell population cultured in the presence of a test substance is equivalent to or lower than the low-immunogenicity control level, the immunogenicity of the test substance can be evaluated to be low; or when the proportion is higher than the low-immunogenicity control level, the immunogenicity of the test substance can be evaluated to be high.

In another embodiment of the present invention, the proportion of IL-2-secreting T cells in a cell population cultured in the presence of a substance that has been found to have high immunogenicity by another immunogenicity evaluation method (for example, a drug having high anti-drug antibody incidence in a clinical trial or a substance having high $CD4^+$ T cell proliferation-inducing ability) can be used as a control level in evaluating immunogenicity. This control level can be referred to as "high-immunogenicity control level". In that case, when the proportion of IL-2-secreting T cells in a cell population cultured in the presence of a test substance is equivalent to or higher than the high-immunogenicity control level, the immunogenicity of the test substance can be evaluated to be high; or when the proportion is lower than the high-immunogenicity control level, the immunogenicity of the test substance can be evaluated to be not high.

In the context of the present invention, a substance known to have low immunogenicity and a substance known to have high immunogenicity may be substances that have been evaluated in advance for their immunogenicity by the evaluation method of the present invention, or they may be substances known to have high or low immunogenicity based on anti-drug antibody incidence in a clinical trial (clinical ADA incidence) or $CD4^+$ T cell proliferation-inducing ability, which is a known immunogenicity indicator. An example of a substance known to have low immunogenicity (but not limited to this example) is a protein formulation Enbrel®. An example of a substance known to have high immunogenicity (but not limited to this example) is KLH. Similarly to the indicator of the present invention (proportion of IL-2-secreting T cells), these indicators are relative indicators, and those skilled in the art can appropriately set a high or low (strong or weak) immunogenicity standard according to the purpose. For example, when the clinical anti-drug antibody incidence (appearance frequency) is less than 10%, or preferably less than 5%, the incidence can be evaluated to be low (the immunogenicity can be evaluated to be low). Furthermore, for example, when the incidence is 30% or more, the incidence can be evaluated to be high (the immunogenicity can be evaluated to be high).

In yet another embodiment of the present invention, the proportion of IL-2-secreting T cells in a cell population cultured in the absence of a test substance can be used as a control level in evaluating immunogenicity. This control level can be referred to as "negative control level". In a particular embodiment of the present invention, when the proportion of IL-2-secreting T cells in a cell population cultured in the presence of a test substance is equivalent to or lower than the negative control level, the immunogenicity of the test substance can be evaluated to be low; or when the proportion is higher than the negative control level, the immunogenicity of the test substance can be evaluated to be not low.

Those skilled in the art can set an appropriate control level according to the purpose and evaluate the immunogenicity of a test substance as being present or absent, or high or low (strong or weak) by making a comparison to that level. The immunogenicity of a test substance can also be evaluated by comparing the proportion of IL-2-secreting T cells calculated by the method of the present invention to the multiple control levels described above. Depending on the purpose, immunogenicity can also be evaluated in a relative manner among test substances based on their measured values. Even in that case, it is preferable to use a control level measured under the same conditions as those for culture and IL-2 detection in the presence of each test substance.

In the present invention, when the proportion of IL-2-secreting T cells in a cell population cultured in the presence of a test substance is, for example, 150%, 200%, 250%, or more of the control level, the test substance can be evaluated to have high immunogenicity. Furthermore, when the proportion of IL-2-secreting T cells in a cell population cultured in the presence of a test substance is, for example, 100%, 75%, 50%, or less of the control level, the test substance can be evaluated to have low immunogenicity. Such evaluation standards can be set appropriately according to the type of the control level used, or the purpose for screening.

The present inventors elucidated that the proportion of IL-2-secreting T cells in a cell population cultured in the presence of a test substance correlates with a known immunogenicity indicator (clinical anti-drug antibody incidence) (Table 1). Therefore, the proportion of IL-2-secreting T cells in a cell population cultured in the presence of a test substance can be used as a "relative" evaluation indicator in evaluating immunogenicity. For example, in the process of optimizing candidates for therapeutic antibodies, the proportions of IL-2-secreting T cells in cell populations cultured in the presence of different modified antibodies can be compared with one another, and a modified antibody yielding a relatively low value for the proportion, that is, a modified antibody having relatively low immunogenicity can be selected as a candidate for therapeutic antibody development.

In the screening method of the present invention, if the proportion of IL-2-secreting T cells in a cell population cultured in the presence of a test substance is lower than a predetermined control level (threshold), the test substance can be selected as a candidate substance for pharmaceuticals having low immunogenicity. While the control level may be set according to the purpose for screening, it is preferable to use as the control level the value or range obtained under the same conditions such as the timing of detection of IL-2-secreting T cells. In the method of screening for a pharmaceutical candidate substance, the proportion of IL-2-secreting T cells for a test substance can be compared to a low-immunogenicity control level, which is the proportion of IL-2-secreting T cells in a cell population cultured in the presence of a substance known to have low immunogenicity. In the method of screening for modified antibodies having low immunogenicity during the process for optimizing candidates for therapeutic antibodies, when the proportion of IL-2-secreting T cells in a cell population cultured in the presence of a modified antibody is lower than the proportion for the antibody prior to modification (control level), the substance can be selected as a candidate for therapeutic antibody development. Furthermore, candidate substances can be narrowed down from among many test substances by setting an appropriate value according to the purpose as the control level, such as the median value, upper one-third, or lower one-third of the measurement values resulting from many samples.

The control level is preferably set appropriately according to the conditions for culturing in the presence of a test substance and for detecting IL-2. Furthermore, the donor of a cell population from which a higher proportion of IL-2-secreting T cells than the control level have been detected can be defined as a positive donor, and the proportion of positive donors in the total number of tested donors can be used as an indicator for evaluating immunogenicity. Therefore, methods of the present invention may comprise the step of defining as a positive donor, a donor from whom a higher proportion of IL-2-secreting T cells than the control level have been detected, and using the proportion of positive donors in the total number of donors in the same assay as an indicator for evaluating immunogenicity.

The immunogenicity evaluation method of the present invention specifically comprises the steps of:
(a) culturing a blood-derived cell population with a test substance, wherein the blood-derived cell population comprises antigen-presenting cells (APCs) and CD4+ T cells and does not substantially comprise CD8+ T cells or CD25+ T cells;
(b) detecting IL-2-secreting T cells in the cell population cultured in step (a) at a time point during the early stage of IL-2 secretion; and
(c) calculating the proportion of the IL-2-secreting T cells detected in step (b).

The present invention also relates to use of IL-2-secreting T cells for evaluating immunogenicity of a test substance, and IL-2-secreting T cells for use in evaluating immunogenicity of a test substance. In these inventions, IL-2-secreting cells are preferably IL-2-secreting T cells at a time point during the early stage of IL-2 secretion, more preferably IL-2-secreting T cells before T cell proliferation becomes active, and even more preferably IL-2-secreting T cells 24 hours to 72 hours after initiation of culture in the presence of a test substance.

In the present invention, a "cell population comprising antigen-presenting cells (APCs) and CD4$^+$ T cells" can be referred to as a cell population substantially comprising antigen-presenting cells (APCs) and CD4$^+$ T cells, or a cell population comprising antigen-presenting cells (APCs) and CD4$^+$ T cells at a proportion that can induce immune responses.

In the present invention, a "cell population which does not substantially comprise CD8$^+$ T cells or CD25$^+$ T cells" refers to a cell population in which the proportion of the sum of CD8$^+$ T cells and CD25$^+$ T cells to the total cells is 10% or less, preferably 5% or less, and particularly preferably 1% or less.

In one embodiment, the immunogenicity evaluation method of the present invention further comprises the step of comparing the proportion of IL-2-secreting T cells calculated in step (c) to a control level, wherein it is indicated that the immunogenicity of the test substance is low if the proportion is equivalent to or lower than the control level. In another embodiment, the immunogenicity evaluation method of the present invention further comprises the step of determining that the immunogenicity of the test substance is low if the proportion of IL-2-secreting T cells calculated in step (c) is equivalent to or lower than the control level.

In one embodiment, the immunogenicity evaluation method of the present invention further comprises the step of comparing the proportion of IL-2-secreting T cells calculated in step (c) to a control level, wherein it is indicated that the immunogenicity of the test substance is high if the proportion is equivalent to or higher than the control level. In another embodiment, the immunogenicity evaluation method of the present invention further comprises the step of determining that the immunogenicity of the test substance is high if the proportion of IL-2-secreting T cells calculated in step (c) is equivalent to or higher than the control level. In another embodiment, the immunogenicity evaluation method of the present invention further comprises the step of determining that the immunogenicity of the test substance is high if the proportion of IL secreting T cells calculated in step (c) is significantly higher than the proportion yielded when the culturing step (a) is performed in the absence of the test substance (negative control level). In yet another embodiment, the immunogenicity evaluation method of the present invention further comprises the step of determining that the immunogenicity of the test substance is high if the proportion of IL-2-secreting T cells calculated in step (c) is equivalent to or higher than the proportion yielded when the culturing step (a) is performed in the presence of a substance known to have high immunogenicity (high-immunogenicity control level). In another embodiment, the immunogenicity evaluation method of the present invention further comprises the step of determining that the immunogenicity of the test substance is low if the proportion of IL-2-secreting T cells calculated in step (c) is equivalent to or less than the proportion yielded when the culturing step (a) is performed in the presence of a substance known to have low immunogenicity (low-immunogenicity control level).

The present invention also relates to methods of measuring helper T cell (Th cell) response to a test substance, which methods are for evaluating immunogenicity of the test substance. More specifically, the present invention relates to methods of measuring the proportion of IL-2-secreting CD4$^+$ T cells in a cell population cultured together with a test substance, which methods are for evaluating immunogenicity of the test substance. In an embodiment of the measurement method of the present invention, the cell population is a blood-derived cell population which comprises antigen-presenting cells (APCs) and CD4$^+$ T cells and does not substantially comprise CD8$^+$ T cells or CD25$^+$ T cells. In an embodiment of the measurement method of the present invention, the aforementioned proportion is the proportion of IL-2-secreting CD4$^+$ T cells at a time point during the early stage of IL-2 secretion in the aforementioned cell population. The time point is preferably the timing before proliferation of CD4$^+$ T cells in the cell population becomes active, and is particularly preferably between 24 hours and 72 hours after initiation of the culturing.

The present invention relates to methods for selecting a substance (modified substance) with reduced immunogenicity, or methods for evaluating whether immunogenicity of a modified substance has been reduced. In one embodiment, the method comprises the steps of:

(a) culturing a blood-derived cell population with a modified substance or a non-modified substance, wherein the blood-derived cell population comprises antigen-presenting cells (APCs) and CD4$^+$ T cells and does not substantially comprise CD8$^+$ T cells or CD25$^+$ T cells;
(b) detecting IL-2-secreting T cells in the cell population cultured in step (a) at a time point during the early stage of IL-2 secretion;
(c) calculating the proportion of the IL-2-secreting T cells detected in step (b); and
(d) determining that the immunogenicity of the modified substance has been reduced if the proportion of IL-2-secreting T cells calculated in step (c) when the cell population is cultured with the modified substance is lower than the proportion when the cell population is cultured with the non-modified substance.

In another embodiment of the method, by comparing modified substances with one another, a modified substance with much less immunogenicity can be selected. In such an embodiment, step (d) above is the step of determining that the immunogenicity of a modified substance has been reduced compared to another modified substance if the proportion of IL-2-secreting T cells calculated in step (c) when cultured with the modified substance is lower than the proportion when cultured with said other modified substance.

The present invention also relates to methods of screening for a candidate substance (lead compound) for a pharmaceutical. In one embodiment, the method comprises the steps of:
(a) culturing a blood-derived cell population with a test substance, wherein the blood-derived cell population comprises antigen-presenting cells (APCs) and CD4$^+$ T cells and does not substantially comprise CD8$^+$ T cells or CD25$^+$ T cells;
(b) detecting IL-2-secreting T cells in the cell population cultured in step (a) at a time point during the early stage of IL-2 secretion;
(c) calculating the proportion of the IL-2-secreting T cells detected in step (b); and
(d) selecting the test substance as a pharmaceutical candidate substance if the proportion of IL-2-secreting T cells calculated in step (c) is lower than the control level;

In step (d), the control level to be compared to the proportion of IL-2-secreting T cells calculated in step (c) can be set appropriately according to the purpose of the screening. For example, in the process for optimizing pharmaceutical candidates, a test substance that yields a relatively lower proportion of the IL-2-secreting T cells compared to other test substances can be selected as a candidate substance. Alternatively, a substance that yields a relatively lower proportion of the IL-2-secreting T cells compared to a predetermined control level can be selected as a candidate substance.

The present invention also relates to methods for predicting the response of a subject to immunotherapy with a test substance. In one embodiment, the method comprises the steps of:
(a) culturing a cell population with a test substance, wherein the cell population is derived from blood obtained from a subject, and wherein the cell population comprises antigen-presenting cells (APCs) and CD4$^+$ T cells and does not substantially comprise CD8$^+$ T cells or CD25$^+$ T cells;
(b) detecting IL-2-secreting T cells in the cell population cultured in step (a) at a time point during the early stage of IL-2 secretion;
(c) calculating the proportion of the IL-2-secreting T cells detected in step (b); and
(d) determining that the responsiveness of the subject to immunotherapy with the test substance is high if the proportion of IL-2-secreting T cells calculated in step (c) is higher than a control level.

The present invention also relates to kits for evaluating immunogenicity of a test substance. In addition to an IL-2-detection reagent, the kit optionally comprises a control substance with a known level of immunogenicity. The kit of the present invention can comprise a high-immunogenicity control substance known to have high immunogenicity and a low-immunogenicity control substance known to have low immunogenicity. The kit of the present invention can comprise a package insert describing the timing and such suitable for detection of IL-2-secreting T cells in a cell population cultured in the presence of a test substance.

EXAMPLES

Herein below, the present invention will be described in detail with reference to the Examples, but it is not to be construed as being limited thereto.

Materials and Methods

Thawing Frozen PBMCs

Frozen PBMCs (Lonza) were thawed at 37° C., and washed with a medium at room temperature to remove DMSO from the cell suspension. After washing, the cells were counted to prepare a 1×10$^7$ cells/mL cell suspension.

Sorting CD8$^-$ PBMCs

To the 1×10$^7$ cells/mL PBMC suspension, a necessary amount of Dynabeads™ CD8 (25 µL/10$^7$ PBMCs) was added. After making the cells and beads homogeneous through mixing by inversion, they were allowed to react with shaking at 4° C. in the dark for 30 minutes. After completion of the reaction, the beads were removed to collect the CD8$^-$ PBMC suspension. Upon centrifugation and removal of the supernatant, the cells were counted to prepare a 2.5×10$^7$ cells/mL cell suspension.

Sorting CD8$^-$CD25$^{low}$ PBMCs

To the 2.5×10$^7$ cells/mL CD8-PBMC suspension, a necessary amount of Dynabeads™ CD25 (25 µL/2.5×10$^7$ CD8$^-$ PBMCs) was added. After making the cells and beads homogeneous through mixing by inversion, they were allowed to react with shaking at 4° C. in the dark for 30 minutes. After completion of the reaction, the beads were removed to collect the CD8$^-$CD25$^{low}$ PBMC suspension. Upon centrifugation and removal of the supernatant, the cells were counted to prepare a 1×10$^6$ cells/mL cell suspension. The cell suspension was seeded at 1 mL/well in a 24-well flat-bottomed plate and preincubated at 37° C. in a 5% CO$_2$ incubator for one hour before adding the test substance or the positive control substance.

Test Substance Addition and Cell Culturing

A test substance or a positive control was added to the preincubated cells, and the cells were cultured at 37° C. in a 5% CO$_2$ incubator for various periods of time.

IL-2 Secretion Assay

After culturing in the presence or absence of a test substance or a positive control substance, 10 µL of IL-2 catch reagent (IL-2 secretion assay kit, Miltenyi Biotec) was added to each well, and the cells were incubated at 37° C. in a 5% CO$_2$ incubator for one hour. Subsequently, the cell suspension was collected and subjected to centrifugation at 4° C. for culture medium removal and washing. The washed cells were made into 150 µL of a cell suspension using a flow cytometry washing/staining solution at 4° C. on ice, then mixed with an antibody mixture solution (anti-CD3 antibody (BD), anti-CD4 antibody (BD), and anti-CD14 antibody (BD), and IL-2 Detection Antibody (IL-2 secretion assay kit, Miltenyi Biotec)) in a 96-well round-bottomed plate, and then stained at 4° C. in the dark for 30 minutes. This was followed by removal of unreacted antibodies and washing, and the washed cells were subjected to nuclear staining using 7AAD (7-Amino-Actinomycin D) in the dark for three minutes at room temperature.

The stained cells were subjected to flow cytometry measurements under conditions where the maximum number of measurements in the lymphocyte gate is 200000.

Measurement of Anti-Drug Antibody Incidence in a Clinical Trial

Appearance of anti-drug antibodies (ADA) against each of the test substances was measured by the method set forth below, and the frequency (incidence) of donors from whom ADA appearance has been detected was calculated.

Antibody A: ECL method; Enbrel® and ReoPro®: ELISA method; and hA33: Biacore® method.

Example 1

Search for an Early-Stage Marker Suitable for Evaluating Immunogenicity.

1-1. Analysis of the Proportion of IL-2-Secreting $CD4^+$ T Cells Before the Cells Exhibit Active Antigen-Specific Proliferation.

Figure 1:
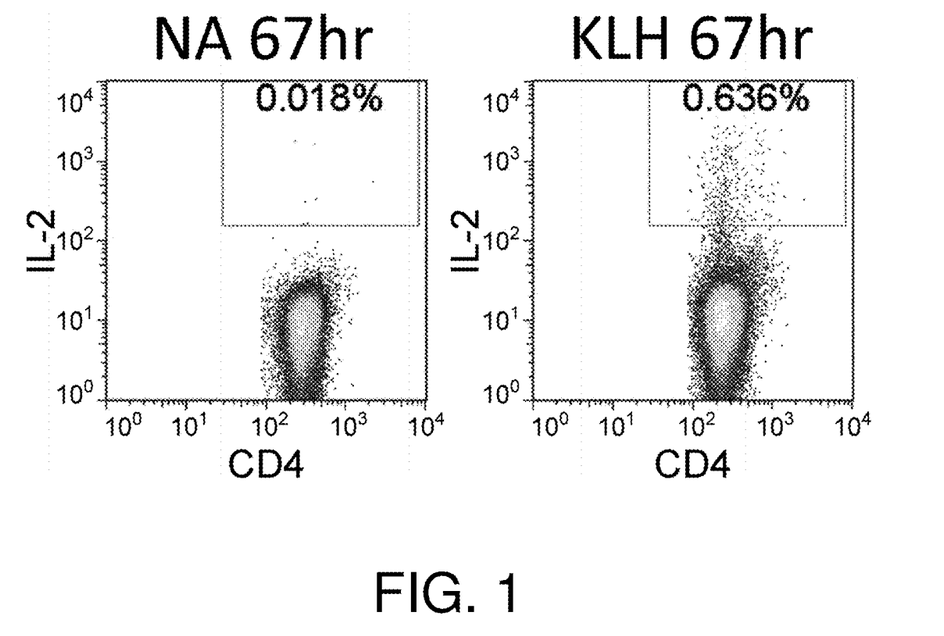
FIG. 1 presents diagrams showing the results of analyzing by flow cytometry the proportion of IL-2-secreting $CD4^+$ T cells in $CD8^-CD25^{low}$ PBMCs cultured for 67 hours in the presence or absence of Keyhole limpet hemocyanin (KLH) (100 μg/mL/well). NA (No Ag: no antigen) shows the result from the negative control when culturing was performed in the absence of the test substance.
Figure 2:
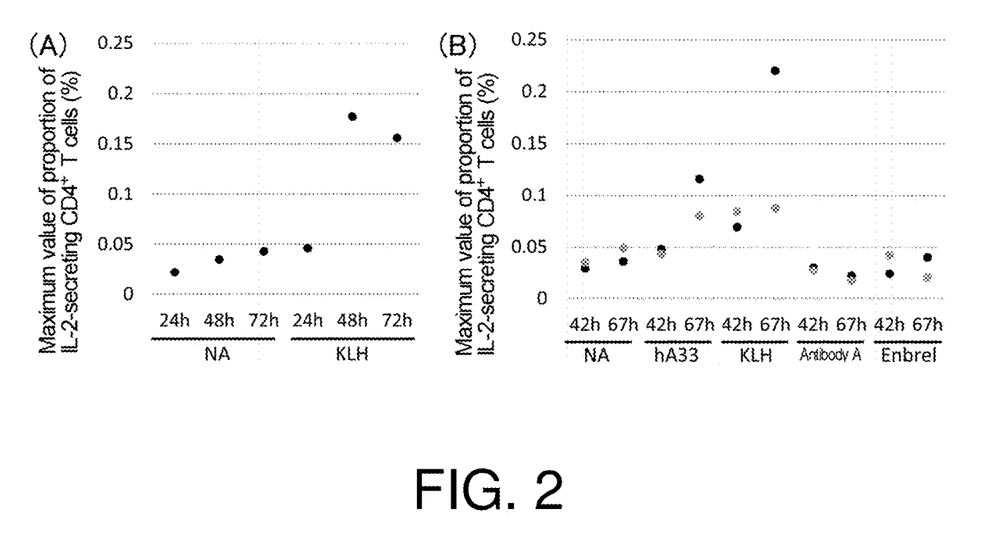
FIG. 2 presents charts showing the maximum values of the proportions of IL-2-secreting $CD4^+$ T cells in $CD8^-CD25^{low}$ PBMCs cultured for 24 hours to 72 hours in the presence of each of the various test substances (100 μg/mL/well). The data shows the results for the respective donors from whom the used PBMCs are derived. NA (No Ag: no antigen) shows the results from the negative control when culturing was performed in the absence of a test substance.

Proportions of the IL-2-secreting $CD4^+$ T cell subset in a population of $CD8^-CD25^{low}$ PBMCs stimulated with an immune-stimulating substance for various periods of time were analyzed. Specifically, IL-2-secreting $CD4^+$ T cells in a population of $CD8^-CD25^{low}$ PBMCs cultured in the presence of KLH for 24 hours to 72 hours were detected using an IL-2 catch reagent and an IL-2 Detection Antibody (IL-2 secretion assay kit, Miltenyi Biotec), and the proportion of IL-2-secreting $CD4^+$ T cells in a population of $CD8^-CD25^{low}$ PBMCs was analyzed by flow cytometry. As shown in FIGS. 1 and 2, when culturing was performed in the presence of KLH for 42 hours, 48 hours, 67 hours, and 72 hours, higher proportion of IL-2-secreting T cells were detected compared to when the culturing was performed in the absence of the immune-stimulating substance (NA) for the same periods of time. Among them, particularly high proportion of IL-2-secreting T cells were detected when culturing was performed in the presence of KLH for 67 hours, and similar results were obtained when culturing was performed in the presence of an anti-hA33 antibody known to have relatively high immunogenicity. Anti-hA33 antibodies can be produced by those skilled in the art, for example, by referring to the description in WO1994/013805. On the other hand, even at these time points, the proportions of IL-2-secreting T cells detected when culturing was performed in the presence of Enbrel®, a commercially available pharmaceutical known to have low immunogenicity were at the same level as when culturing was performed in the absence of an immune-stimulating substance (NA) for the same periods of time. These results show that after stimulation with a test substance, the proportion of IL-2-secreting $CD4^+$ T cells at a time point before active proliferation is exhibited can be used as an early-stage marker for evaluating immunogenicity of a test substance.

Example 2

Comparison Between ADA Incidence and the Proportion of IL-2-Secreting $CD4^+$ T Cells Before Active Antigen-Specific Proliferation is Exhibited by Immune Response 2-1. Evaluation of Immunogenicity of Protein Formulations Using as an Indicator the Proportion of IL-2-Secreting $CD4^+$ T Cells Before Active Antigen-Specific Proliferation is Exhibited.

Proportions of IL-2-secreting $CD4^+$ T cells before active proliferation is exhibited when various protein formulations including commercially available pharmaceuticals were used as the immune-stimulating substances were analyzed. Specifically, from frozen PBMCs derived from 16 to 31 donors (HLA-DRB1 coverage: 70% Caucasian, and 60% Japanese), which were purchased from LONZA, $CD8^-CD25^{low}$ PBMCs were prepared at $1\times10^6$ cells/mL in OpTmizer™ CTS™ T-cell Expansion SFM (Gibco), seeded at 1 mL/well into a 24-well flat-bottomed plate, and preincubated at 37° C. in a 5% $CO_2$ incubator for one hour. Subsequently, various test substances were added, and culturing was performed for 67 hours. IL-2-secreting cells in the cultured cell population were labeled by adding a Miltenyi Biotec IL-2 catch reagent (IL-2 secretion assay kit, Miltenyi Biotec) at 10 µL/well into the culture medium, and then culturing for one more hour. Then, the cultured $CD8^-CD25^{low}$ PBMCs were collected at room temperature and centrifuged at 4° C. to remove the supernatant. The cells were suspended in a washing/staining solution for flow cytometry at 4° C. on ice, transferred into a 96-well round-bottomed plate, and then washed. After staining with an anti-CD3 antibody (BD), anti-CD4 antibody (BD), and anti-CD14 antibody (BD), and IL-2 Detection Antibody (IL-2 secretion assay kit, Miltenyi Biotec), the cells were washed. After adding 7AAD, the cells were subjected to flow cytometry, and the proportions of IL-2-secreting $CD4^+$ T cells were determined. The results are shown in FIG. 3.

Figure 3:
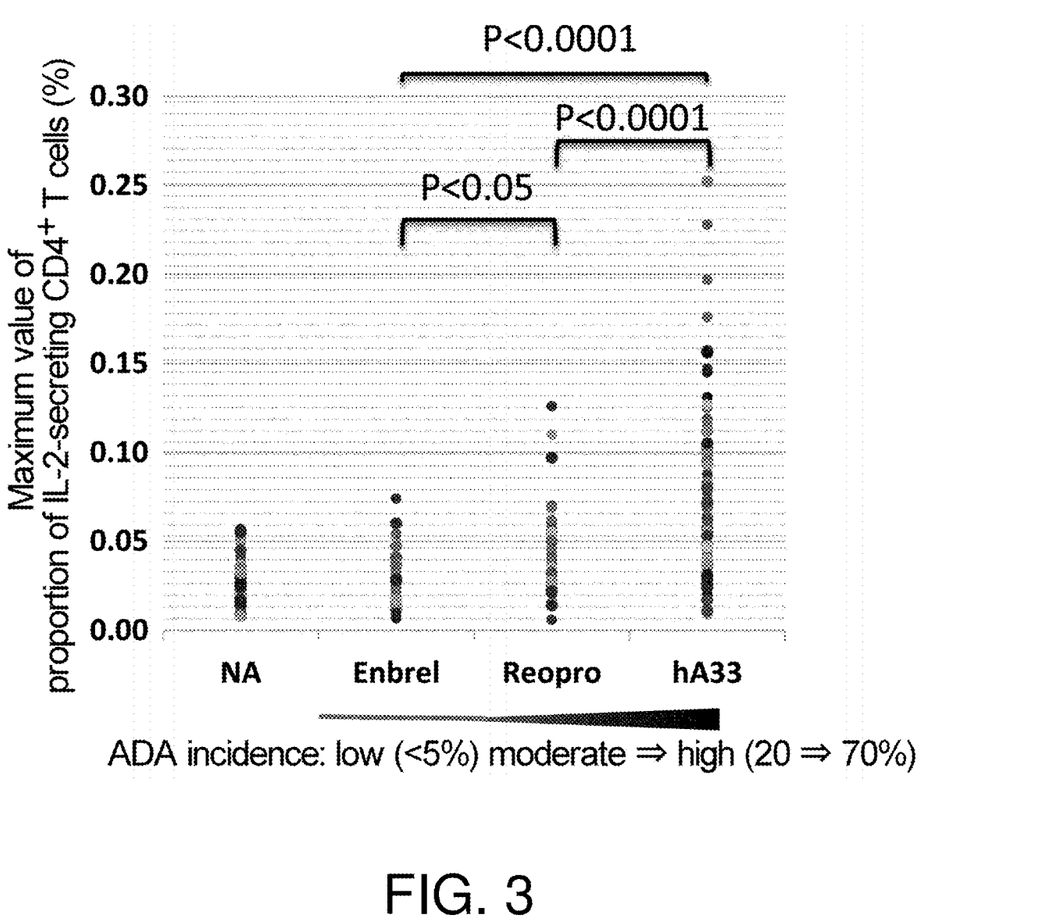
FIG. 3 is a chart showing the maximum values of the proportions of IL-2-secreting $CD4^+$ T cells in $CD8^-CD25^{low}$ PBMCs cultured for 67 hours in the presence of each of the various test substances (100 μg/mL/well). The data shows the results for the respective donors from whom the used PBMCs are derived. NA (No Ag: no antigen) shows the result from the negative control when culturing was performed in the absence of a test substance.

As shown in FIG. 3, for many donors' PBMCs, culturing in the presence of the anti-hA33 antibody known to have relatively high immunogenicity resulted in detection of high proportions of IL-2-secreting $CD4^+$ T cells. Next, when culturing was performed in the presence of a commercially available pharmaceutical ReoPro®, high proportions of IL-2-secreting $CD4^+$ T cells were detected for PBMCs derived from multiple donors. On the other hand, when culturing was performed in the presence of Enbrel®, which is the aforementioned commercially available pharmaceutical known to have low immunogenicity, there were only a few cases where higher proportions of IL-2-secreting $CD4^+$ T cells were detected compared to that of a negative control (NA) cultured in the absence of the test substance. These results are shown in Table 1 together with the clinical anti-drug antibody (ADA) incidence, which is the conventional immunogenicity evaluation method.

TABLE 1

| | Evaluation items | NA | Enbrel | Reopro | hA33 | KLH |
|---|---|---|---|---|---|---|
| Proportion of IL-2-secreting $CD4^+$ T cells | Total number of donors | 31 | 21 | 16 | 31 | 21 |
| | Number of positive donors | 0 | 1 | 3 | 21 | 21 |
| | Frequency of positive donors | 0 | 4.8 | 18.8 | 67.7 | 100.0 |
| | ADA incidence | | 6% | 27% | 33-73% | — |

In Table 1, the results are shown in order from the test substance yielding the lowest ADA incidence. This order corresponded to the order of the proportions of IL-2-secreting CD4+ T cells shown in FIG. 3. Specifically, for ReoPro® and anti-hA33 antibody which showed high proportions of IL-2-secreting CD4+ T cells in FIG. 3, clinical ADA incidences were high, correlating with the proportions. On the other hand, for Enbrel® showing low proportion of IL-2-secreting CD4+ T cells, the ADA incidence was low.

Table 1 shows the numbers and proportions of PBMC donors evaluated to be positive when the proportion of IL-2-secreting CD4+ T cells higher than that of the non-stimulating negative control (NA) is set to 0.07% or more. As a result of the evaluation by a t-test using this proportion as the evaluation indicator, it was evaluated that a significantly larger number of IL-2-secreting CD4+ T cells were detected for the anti-hA33 antibody than for Enbrel® and ReoPro®. Screening for pharmaceutical candidate substances can be performed, for example, by setting the control level to approximately 20% to 60%, approximately 20% to 50%, approximately 20% to 40%, approximately 20% to 30%, or such, which is a level between the positive donor frequency for ReoPro® and the positive donor frequency for the anti-hA33 antibody when the proportion of IL-2-secreting CD4+ T cells is set to 0.07% or more.

Figure 4:
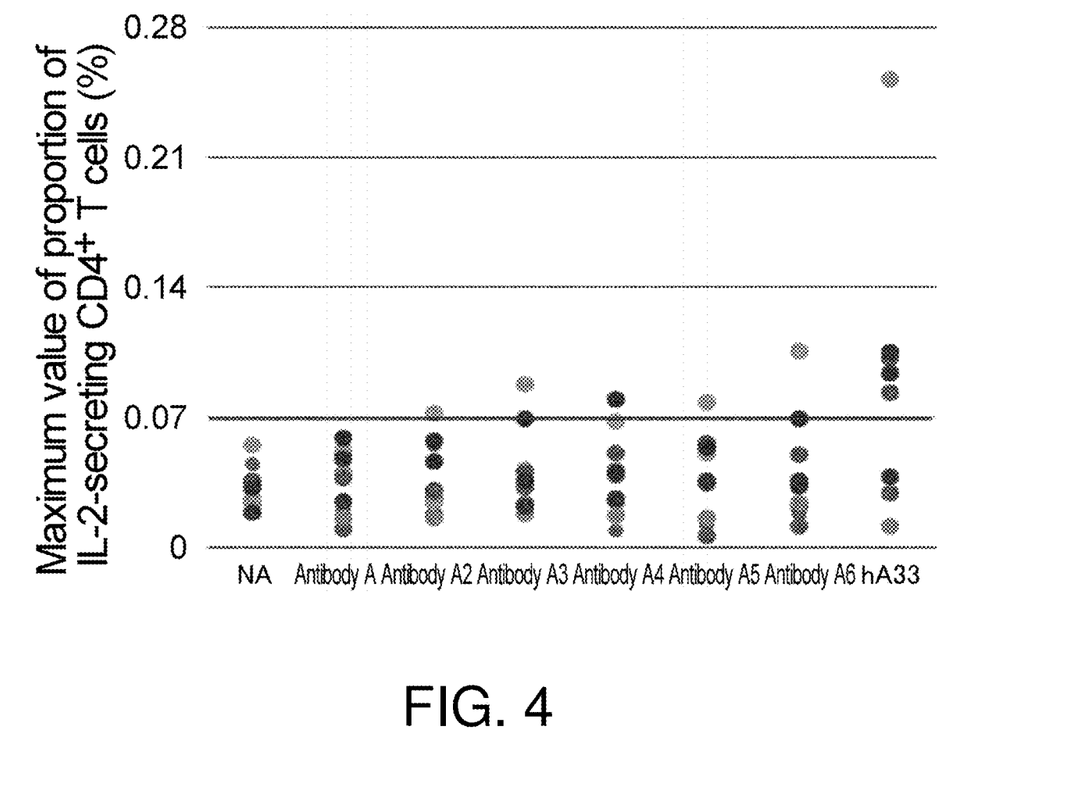
FIG. 4 is a chart showing the maximum value of the proportion of IL-2-secreting $CD4^+$ T cells in $CD8^-CD25^{low}$ PBMCs cultured for 67 hours in the presence of each of the various test substances (100 μg/mL/well). The data shows the maximum values of the proportions of IL-2-secreting $CD4^+$ T cells for the respective donors from whom the used PBMCs are derived. NA (No Ag: no antigen) shows the result from the negative control when culturing was performed in the absence of a test substance.

2-2. Evaluation of Immunogenicity of Modified Antibodies Using as an Indicator the Proportion of IL-2-Secreting CD4+ T Cells Before Active Antigen-Specific Proliferation is Exhibited Next, the immunogenicity of multiple different types of modified antibodies sharing a common binding target were evaluated by using as an indicator the proportion of IL-2-secreting CD4+ T cells before active proliferation is exhibited. Specifically, CD8−CD25$^{low}$ PBMCs were prepared from frozen PBMCs derived from ten donors, and the cells were cultured for 67 hours in the presence of antibody A, antibodies A2 to A6 which are modified forms thereof, and the anti-hA33 antibody known to have high immunogenicity. FIG. 4 shows the results of determining the proportions of IL-2-secreting cells in the cultured cell populations as in Example 2-1.

As shown in FIG. 4, even for the series of modified forms binding to the same target, each modified form resulted in a different proportion of IL-2-secreting CD4+ T cells being detected before the active proliferation was exhibited. For these results, Table 2 shows the proportions of PBMC donors evaluated to be positive when the proportion of IL-2-secreting CD4+ T cells higher than that of antibody A is set to 0.07% or more. When evaluated based on this proportion, the frequencies of positive donors for antibodies A2 to A6 were slightly high compared to that for antibody A, but was sufficiently low compared to that for anti-hA33 antibody. Therefore, using the proportion of IL-2-secreting CD4+ T cells before active proliferation as the indicator, modified forms not having high immunogenicity can be selected from among the various modified forms as pharmaceutical candidate substances. Use of such an evaluation system allows, for example, screening based on immunogenicity in an optimization process for therapeutic antibody candidates to be performed in a short span of time.

TABLE 2

|  | Proportion of IL-2-secreting CD4+T Cells (number of positive donors/number of donors) |
| --- | --- |
| Antibody A | 0/10 |
| Antibody A2 | 1/10 |
| Antibody A3 | 1/10 |
| Antibody A4 | 1/10 |
| Antibody A5 | 1/10 |
| Antibody A6 | 1/10 |
| Anti-hA33 antibody | 7/10 |

The results shown in Tables 1 and 2 indicated that (1) evaluation results equivalent to those when ADA incidence is used as the indicator can be obtained by using the proportion of IL-2-secreting CD4+ T cells before active proliferation is exhibited as the indicator; and (2) an appropriate control level to be set according to the conditions of the evaluation system (for example, the timing of detection of IL-2-secreting CD4+ T cells after stimulation with a test substance) is useful in screening to select test substances with low immunogenicity as candidate substances for pharmaceutical development.

Example 3

Figure 5:
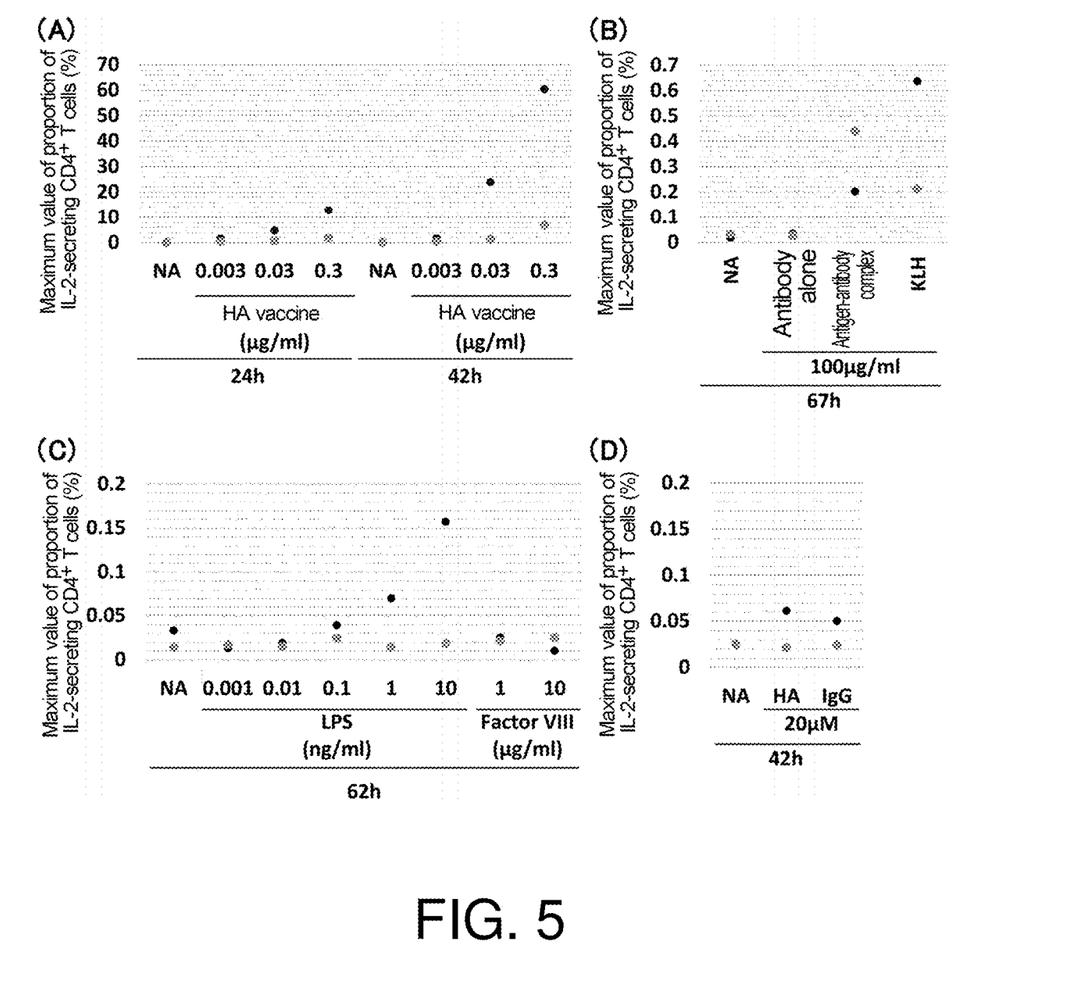
FIG. 5 presents charts showing the maximum values of the proportions of IL-2-secreting $CD4^+$ T cells in $CD8^-CD25^{low}$ PBMCs cultured for 24 hours to 67 hours in the presence of (A) influenza HA vaccine, (B) an antibody alone or an antigen-antibody complex, (C) LPS or Factor VIII, or (D) an HA peptide or an IgG peptide. The data shows the results for the respective donors from whom the used PBMCs are derived. NA (No Ag: no antigen) shows the result from the negative control when culturing was performed in the absence of a test substance.

Evaluation of Immunogenicity of Various Test Substances Using as an Indicator the Proportion of IL-2-Secreting CD4+ T Cells Before Active Proliferation Various test substances were evaluated for their immunogenicity using the evaluation indicator of the present invention (proportion of IL-2-secreting CD4+ T cells before active proliferation of T cells), which was found in Example 2 to yield the evaluation results equivalent to the results using a known indicator for immunogenicity evaluation, ADA incidence. Specifically, a vaccine (influenza HA vaccine: FIG. 5A), antibody B or a complex of antibody B and its antigen (FIG. 5B), or an impurity which may contaminate a protein formulation (endotoxin (LPS): FIG. 5C) was used as the test substance, and the proportion of IL-2-secreting CD4+ T cells before active proliferation was determined as in Example 2. The results are shown in FIG. 5.

As shown in FIG. 5A, when cells were cultured in the presence of influenza HA vaccine known to have very high immunogenicity, IL-2-secreting CD4+ T cells were clearly detected at vaccine concentrations of 0.003 μg/mL or more.

Furthermore, when cells were cultured in the presence of KLH having high immunogenicity, which is used as a carrier protein for immunization, IL-2-secreting CD4+ T cells were definitely detected. When the antibody alone was used as the test substance, which antibody may be used as a low-immunogenicity protein formulation, IL-2-secreting CD4+ T cells were hardly detected; and when a complex formed of the antibody and its antigen was used as the test substance, IL-2-secreting CD4+ T cells were detected (FIG. 5B).

When cells were cultured in the presence of various concentrations of endotoxin (LPS), which is as an example of an impurity which may contaminate a protein formulation, IL-2-secreting CD4+ T cells were definitely detected at LPS concentrations of 0.1 ng/mL and above (FIG. 5C). On the other hand, when blood coagulation factor VIII (Factor VIII) as an example of a blood component was used as the test substance, IL-2-secreting CD4+ T cells could not be definitely detected even at Factor VIII concentration of 10 μg/mL (FIG. 5C).

When a peptide having a smaller molecular weight than a protein was used as the test substance, very few IL-2-secreting CD4+ T cells were detected, as shown in FIG. 5D.

Therefore, the immunogenicity evaluation method of the present invention was found to be applicable to various test substances, and not limited to proteins.

INDUSTRIAL APPLICABILITY

The immunogenicity evaluation method of the present invention is characterized by using as an evaluation indicator the proportion of IL-2-secreting CD4$^+$ T cells detected at a time point during the early stage of IL-2 secretion. More specifically, the method is characterized by using as an evaluation indicator the proportion of IL-2-secreting CD4$^+$ T cells detected at a time point before the proliferation of CD4$^+$ T cells becomes active in response to stimulation with a test substance. Generally, the proportion of a pre-existing T cell repertoire that specifically responds to an antibody pharmaceutical is very low, ranging from 0.01 to 0.3 cells per $10^6$ CD4$^+$ T cells on average. Therefore, immunogenicity had been considered difficult to evaluate at a time point during the period when the proliferation is weakly induced by the test substance (less than five days or preferably 24 hours to 72 hours after initiation of culture in the presence of the test substance) since activation or proliferation of the cells can hardly be detected at the protein level. It was thus common technical knowledge that the secretion of cytokines at a time point after the proliferation became active through the immune response or the clinical anti-drug antibody (ADA) appearance frequency would be used as an indicator for immunogenicity evaluation. In fact, even when an anti-hA33 antibody known to have relatively high immunogenicity was used for stimulation, the proportion of IL-2-secreting CD4$^+$ T cells before the cell proliferation became active was at most 0.25% (FIG. 3). Generally, evaluation systems with such a low frequency of positivity often have poor stability. However, surprisingly, a test substance that had been shown to be less immunogenic than the anti-hA33 antibody according to the clinical anti-drug antibody (ADA) appearance frequency was stably shown to be less immunogenic than the anti-hA33 antibody even according to the proportion of IL-2-secreting CD4$^+$ T cells before the proliferation became active, and its results correlated well with the evaluation results using the conventional evaluation indicator (Table 1). This stable data obtainment despite the low frequency of positivity at a time point during the early stage of IL-2 secretion is considered to be because of the ingenuities provided in the evaluation method, such as the substantial absence of CD8$^+$ T cells and CD25$^+$ T cells in the cell population cultured together with a test substance (CD8$^+$ T cells and CD25$^+$ T cells may be removed in advance from the cell population), the reduction of noises by devising the culturing method (the number of cells and the type of medium), and the ingenious ways of using an IL-2 catch reagent and an IL-2 Detection Antibody to allow highly active T cells to remain.

As described above, the immunogenicity evaluation method of the present invention is useful in that it can evaluate the immunogenicity of test substances such as protein formulations (for example, antibody pharmaceuticals) in a shorter period of time than previously known. Use of the method of the present invention having this advantage can realize high throughput in screening for pharmaceutical candidate substances, and this can contribute to accelerated development of pharmaceuticals.

The invention claimed is:

1. A method for evaluating immunogenicity of a test substance, the method comprising the steps of:
   (a) providing a population of peripheral blood mononuclear cells (PBMCs) from which population CD8$^+$ T cells or CD25$^+$ T cells have been depleted;
   (b) culturing the population of cells with a test substance; and
   (c) measuring the proportion of IL-2-secreting CD4+ T cells in the cell population cultured in step (b) between 24 hours and 72 hours after initiation of the culturing.

2. The method of claim 1, wherein the PBMCs are human PBMCs.

3. The method of claim 1, wherein the test substance is selected from the group consisting of a protein, a peptide, a nucleic acid, a carbohydrate, a lipid, a vaccine, and a conjugate of two or more thereof, and a mixture comprising a combination of two or more thereof.

4. The method of claim 1, wherein the test substance is a protein.

5. The method of claim 1, wherein the test substance is an antibody.

6. The method of claim 1, wherein the measuring the proportion of the IL-2-secreting CD4+ T cells comprises measuring the number of the cells by flow cytometry.

7. The method of claim 3, wherein the measuring the proportion of the IL-2-secreting CD4+ T cells comprises measuring the number of the cells by flow cytometry.

8. The method of claim 2, wherein the test substance is selected from the group consisting of a protein, a peptide, a nucleic acid, a carbohydrate, a lipid, a vaccine, and a conjugate of two or more thereof, and a mixture comprising a combination of two or more thereof.

9. The method of claim 2, wherein the measuring the proportion of the IL-2-secreting CD4+ T cells comprises measuring the number of the cells by flow cytometry.

10. The method of claim 8, wherein the measuring the proportion of the IL-2-secreting CD4+ T cells comprises measuring the number of the cells by flow cytometry.

* * * * *